US010878237B2

(12) United States Patent
Rougeaux et al.

(10) Patent No.: US 10,878,237 B2
(45) Date of Patent: Dec. 29, 2020

(54) SYSTEMS AND METHODS FOR PERFORMING EYE GAZE TRACKING

(71) Applicant: SEEING MACHINES LIMITED, Fyshwick (AU)

(72) Inventors: Sebastien Rougeaux, O'Connor (AU); Timothy James Henry Edwards, Kallista (AU)

(73) Assignee: SEEING MACHINES LIMITED, Fyshwick (AU)

(*) Notice: Subject to any disclaimer, the term of this patent is extended or adjusted under 35 U.S.C. 154(b) by 118 days.

(21) Appl. No.: 16/313,327

(22) PCT Filed: Jun. 14, 2017

(86) PCT No.: PCT/AU2017/050591

§ 371 (c)(1),
(2) Date: Dec. 26, 2018

(87) PCT Pub. No.: WO2018/000020

PCT Pub. Date: Jan. 4, 2018

(65) Prior Publication Data

US 2019/0156100 A1 May 23, 2019

(30) Foreign Application Priority Data

Jun. 29, 2016 (AU) ................................ 2016902546

(51) Int. Cl.
*G06T 7/73* (2017.01)
*G06F 3/01* (2006.01)
*G06K 9/00* (2006.01)

(52) U.S. Cl.
CPC ........... *G06K 9/0061* (2013.01); *G06F 3/013* (2013.01); *G06K 9/00228* (2013.01);
(Continued)

(58) Field of Classification Search
None
See application file for complete search history.

(56) References Cited

U.S. PATENT DOCUMENTS 7,043,056 B2 5/2006 Edwards et al.
8,885,882 B1 11/2014 Yin et al.
(Continued)

FOREIGN PATENT DOCUMENTS

EP 2857939 4/2015
WO 2008141460 11/2008
WO 2015/027289 3/2015

OTHER PUBLICATIONS

Villanueva, et al. | Geometry Issues of Gaze Estimation. Advances in Human-Computer Interaction, by IntechOpen, 2008, pp. 513-534.

(Continued)

*Primary Examiner* — Idowu O Osifade
(74) *Attorney, Agent, or Firm* — Jason P. Mueller; FisherBroyles, LLP

(57) ABSTRACT

A method includes: capturing, from one or more imaging devices, a sequence of time separated images of the subject's face including one or both of the subject's eyes; processing the images to detect specular reflections present in the images, and determining a two dimensional position of any detected specular reflections; characterizing the detected specular reflections into corneal reflections and non-corneal reflections; upon detection of at least one corneal reflection, performing a first eye gaze tracking procedure based on the relative positions of the at least one corneal reflection and at least one reference eye feature; upon detection of no corneal reflections, performing a second eye gaze tracking procedure on one or both eyes of the subject based on the estimation of head pose of the subject; and outputting eye
(Continued)

300
301 System and eye calibration routines
302 Capture images of a subject's face
303 Process the captured images to detect specular reflections in the images and determine a 2D transverse position of each detected specular reflection
304 Characterize the specular reflections into corneal reflections and non-corneal reflections
305 Are corneal reflections detected? Yes / No
306 Perform eye gaze tracking routine A using corneal reflections and 2D iris center position
307 Perform eye gaze tracking routine B using 3D head pose and 2D iris position
308 Output eye gaze vectors gaze vectors of one or both eyes from the first or second eye gaze tracking procedure.

20 Claims, 9 Drawing Sheets

(52) U.S. Cl.
CPC ..... *G06K 9/00597* (2013.01); *G06K 9/00604* (2013.01); *G06T 7/73* (2017.01); *G06T 2207/10021* (2013.01); *G06T 2207/10028* (2013.01)

(56) References Cited

U.S. PATENT DOCUMENTS

2003/0169907 A1* 9/2003 Edwards ............ G06K 9/00281
382/118
2012/0147328 A1 6/2012 Yahav
2012/0219180 A1* 8/2012 Mehra ................ G06K 9/00335
382/103
2016/0026246 A1* 1/2016 Strupczewski ......... G06T 17/10
345/420
2016/0202756 A1* 7/2016 Wu ......................... G06F 3/013
382/103
2016/0210497 A1 7/2016 Rougeaux
2017/0007120 A1* 1/2017 Shudo .................. A61B 3/0025
2017/0083087 A1* 3/2017 Plummer ........... G06K 9/00845

OTHER PUBLICATIONS

Hennessey et al. | A single camera eye-gaze tracking system with free head motion. Proceedings of the 2006 symposium on Eye tracking research & applications, San Diego, California, Mar. 27-29, 2006, pp. 87-94.

Ioannou et al. | Circle recognition through a 2D Hough transform and radius histogramming. Image and vision computing, 17(1999), pp. 15-26.

* cited by examiner

SYSTEMS AND METHODS FOR PERFORMING EYE GAZE TRACKING

This application is a National Stage Entry under 35 U.S.C. 371 of PCT Patent Application No. PCT/AU2017/050591, filed Jun. 14, 2017, which claims priority to Australian Patent Application No. 2016902546, filed Jun. 29, 2016, the entire contents of which are incorporated herein by reference.

FIELD

The present disclosure relates to eye gaze tracking. In particular, the disclosure relates to a hybrid method of calculating eye gaze vector of a subject according to different eye tracking routines for applications such as a vehicle driver drowsiness and attention monitoring systems. While some embodiments will be described herein with particular reference to that application, it will be appreciated that the disclosure is not limited to such a field of use, and is applicable in broader contexts.

BACKGROUND

Any discussion of the background art throughout the specification should in no way be considered as an admission that such art is widely known or forms part of common general knowledge in the field.

Eye gaze tracking is an important measurement in various applications including sports training, cognitive and neurological studies, marketing research and vehicle driver attention monitoring systems. Most common eye gaze tracking methods are performed remotely using video-based eye tracker systems in which one or more cameras capture images of the subject's eye or eyes illuminated by one or more light sources and image processing is performed on the captured images to derive eye position and gaze direction.

In one video-based technique, eye gaze direction is calculated by detecting the position of corneal reflections of the light source (known as 'glints') in conjunction with detecting the pupil location in the images. Glints (also known as "first Purkinje images") are virtual images of light sources that illuminate the eye and are created by a reflection from the front surface of the cornea. The optical properties of the cornea mean that it is at least partially reflective at infrared and near-infrared wavelengths, operating as a convex mirror. With knowledge of the positions of the camera and light source, these detected points can be projected onto a geometric model of the eyeball to derive an estimate of eye gaze direction and optionally a point of gaze if eye gaze vectors can be calculated for both eyes. However, when glints are not present (such as when the subject is looking distant from the camera or is squinting) or difficult to discern, this technique can break down or become inaccurate.

In another video-based technique, the pupil position can be combined with an estimate of pose of the subject's head to derive the eye gaze direction. U.S. Pat. No. 7,043,056 to Edwards et al., assigned to Seeing Machines Pty Ltd and entitled "Facial Image Processing System" (hereinafter "Edwards et al.") discloses such a gaze tracking technique. The head pose estimate is obtained by extracting facial feature points from the captured images and fitting these points to a three dimensional model of a human head. However, this technique is very sensitive to the accuracy of the estimated head pose (including the approximated head size in the model) and the technique becomes very inaccurate when the estimated head pose is slightly incorrect.

US Patent Application Publication 2012/0147328 to Yahav assigned to Microsoft Corporation and entitled "3D Gaze Tracker" (hereinafter "Yahav") relates to a three-dimensional (3D) glint detection-based gaze tracking system that takes into account head orientation to improve accuracy. The technique necessarily requires both conventional two dimensional digital camera and a three dimensional camera. Due to its reliance on glints, this system still breaks down under the relatively common occurrence where glints are not present or difficult to discern.

Therefore, the inventors have identified a desire for more robust eye gaze tracking techniques which operate effectively under varying operating conditions.

SUMMARY

In accordance with a first aspect of the present invention there is provided a method of calculating eye gaze vectors of a subject, the method including:

a) capturing, from one or more imaging devices, a sequence of time separated images of the subject's face including one or both of the subject's eyes;
b) processing the images to detect specular reflections present in the images, and determining a two dimensional position of any detected specular reflections;
c) determining the detected specular reflections to be corneal reflections and non-corneal reflections;
d) upon detection of at least one corneal reflection, performing a first eye gaze tracking procedure based on the relative positions of the at least one corneal reflection and at least one reference eye feature;
e) upon detection of no corneal reflections, determining three dimensional positions of one or more reference facial features of the subject and performing a second eye gaze tracking procedure on one or both eyes of the subject based on the estimation of head pose of the subject from the positions of the one or more detected reference facial features; and
f) outputting eye gaze vectors of one or both eyes from the first or second eye gaze tracking procedure.

Preferably the at least one reference eye feature includes one or more of a pupil center, iris center, pupil/iris boundary or iris/sclera boundary. Preferably the reference facial features of the subject includes a pupil center, iris center, pupil/iris boundary or iris/sclera boundary, eyelids, eye corners, mouth corners, nostrils and ears of the subject.

In one embodiment, determining corneal reflection from the detected specular reflections includes monitoring the two dimensional position of the specular reflections in the sequence and determining detected specular reflections to be corneal reflections when the change in position of the specular reflections between two or more time separated images is less than or equal to a predetermined distance.

In one embodiment the first eye gaze tracking procedure includes:

determining a two dimensional position of at least one reference eye feature;

fitting the two dimensional positions of the corneal reflections and the at least one reference eye feature to a three dimensional cornea model having a known cornea center to determine three dimensional positions of the corneal reflections and iris center; and determining eye gaze vectors for one or both eyes from the three dimensional positions of the corneal reflections and at least one reference eye feature.

In one embodiment the second eye gaze tracking procedure includes:

fitting the three dimensional positions of the one or more reference facial features to a three dimensional head model;

calculating a head pose of the subject including a three dimensional position and three dimensional orientation of the subject's head;

determining a two dimensional position of at least one reference eye feature of one or both eyes of the subject;

fitting the two dimensional position of at least one reference eye feature to a three dimensional eye model having a known eye center within the three dimensional head model to determine three dimensional positions of the at least one reference eye feature;

determine an eye gaze vector for one or both of the eyes from the three dimensional positions of the at least one reference eye feature and eye center.

In one embodiment the method includes the step of estimating the subject's head size from image depth information and inputting this to the three dimensional head model.

In one embodiment the one or more imaging devices include a stereoscopic system of two cameras in which each of the two cameras captures an image at synchronized times during the predetermined period of time. In another embodiment the one or more imaging devices include a time of flight camera. The time of flight camera preferably outputs image data in three dimensions and two dimensional position data is obtained directly from the three dimensional image data. In a further embodiment the one or more imaging devices include a single camera capable of estimating depth in images.

In one embodiment the method includes an initial camera calibration step to calibrate the position and orientation of the one or more imaging devices.

In one embodiment the method includes an initial eye calibration step to calibrate the gaze vectors to account for a fovea offset and/or corneal radius of the subject. Preferably the initial eye calibration step includes capturing images of the subject's face while the subject is observing one or more reference points having a known three dimensional position relative to the one or more imaging devices. Preferably the initial eye calibration is performed using greater than five reference points.

In one embodiment the method includes the step of determining which eye gaze tracking procedure to use based on one or more factors. In one embodiment the factors include a confidence value indicative of the confidence that the reflection detected is a corneal reflection. In another embodiment, the factors include a confidence value indicative of the confidence that the region around the glint has the appearance of an eye. In a further embodiment the factors include a confidence value indicative of a confidence of the head pose. In still another embodiment the factors include a confidence value indicative of a confidence that the region around the facial landmarks has the appearance of a face.

In accordance with a first aspect of the present disclosure there is provided a system for calculating eye gaze vectors of a subject, the system including:

one or more imaging devices configured to capture a sequence of time separated images of the subject's face including one or both of the subject's eyes; and a processor configured to:

process the images to detect specular reflections present in the images;

determining the detected specular reflections to be corneal reflections and non-corneal reflections;

upon detection of at least one corneal reflection, determine a two dimensional position of at least one corneal reflection and a two dimensional position of the at least one reference eye feature of the subject and performing a first eye gaze tracking procedure based on the relative positions of the at least one corneal reflection and the at least one reference eye feature;

upon detection of no corneal reflections, determine three dimensional positions of one or more reference facial features of the subject and performing a second eye gaze tracking procedure on one or both eyes of the subject based on the estimation of head pose of the subject from the positions of the one or more facial features; and output eye gaze vectors of one or both eyes from the first or second eye gaze tracking procedure.

BRIEF DESCRIPTION OF THE DRAWINGS

Embodiments of the disclosure are described, by way of example only, with reference to the accompanying drawings in which.

DETAILED DESCRIPTION

System Overview

The present disclosure relates to an eye gaze tracking system that utilizes multiple different eye gaze tracking routines under different conditions to increase robustness, reliability and accuracy of the tracking. In one embodiment of the disclosure, two eye gaze tracking algorithms are leveraged depending on the detection of corneal reflections ('glints') in the images.

Figure 1:
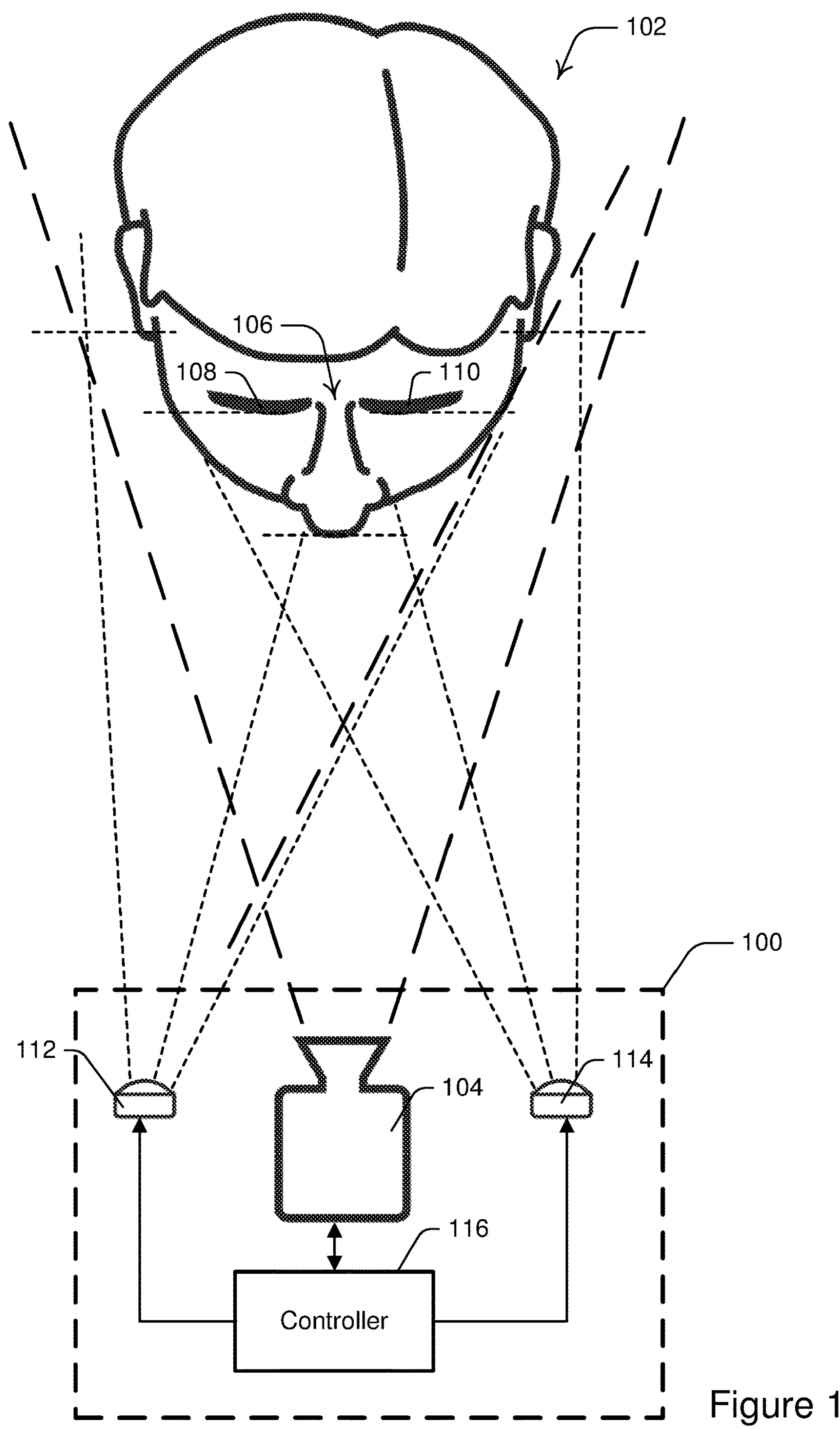
FIG. 1 is a schematic plan view of an eye gaze tracking system according to a first embodiment of the disclosure.

Referring initially to FIG. 1, there is illustrated schematically a system 100 for calculating eye gaze vectors of a subject 102.

System 100 includes an imaging device in the form of a time of flight camera 104 configured to capture time separated images of the subject's face 106 including one or both of the subject's eyes 108 and 110. Time of flight camera 104 captures three dimensional images of the scene within its field of view. Each captured image is stored as a matrix of data representing three dimensions: X and Y dimensions representing the conventional transverse image plane; and a Z dimension representing the depth or range of the objects within the scene at each transverse position. The Z dimension data is obtained by transmitting a pulse of light at the known speed of light and measuring the time taken for the light to reflect off objects within the scene. Objects that are closer to the camera reflect light sooner and thus the reflected light has a shorter 'time of flight' than light reflected off more distant objects. By multiplying the time of flight for each camera pixel by the speed of light, an estimate of the depth or range between the camera and the objects in the scene can be obtained with accuracy in the order of 1 cm. By way of example, FIG. 1 illustrates different depth ranges for the subject's nose, eyes and ears, as illustrated by the horizontal dashed lines. If calibrated correctly, a time of flight camera can record three dimensional data of a three dimensional scene using a single light pulse.

Figure 2:
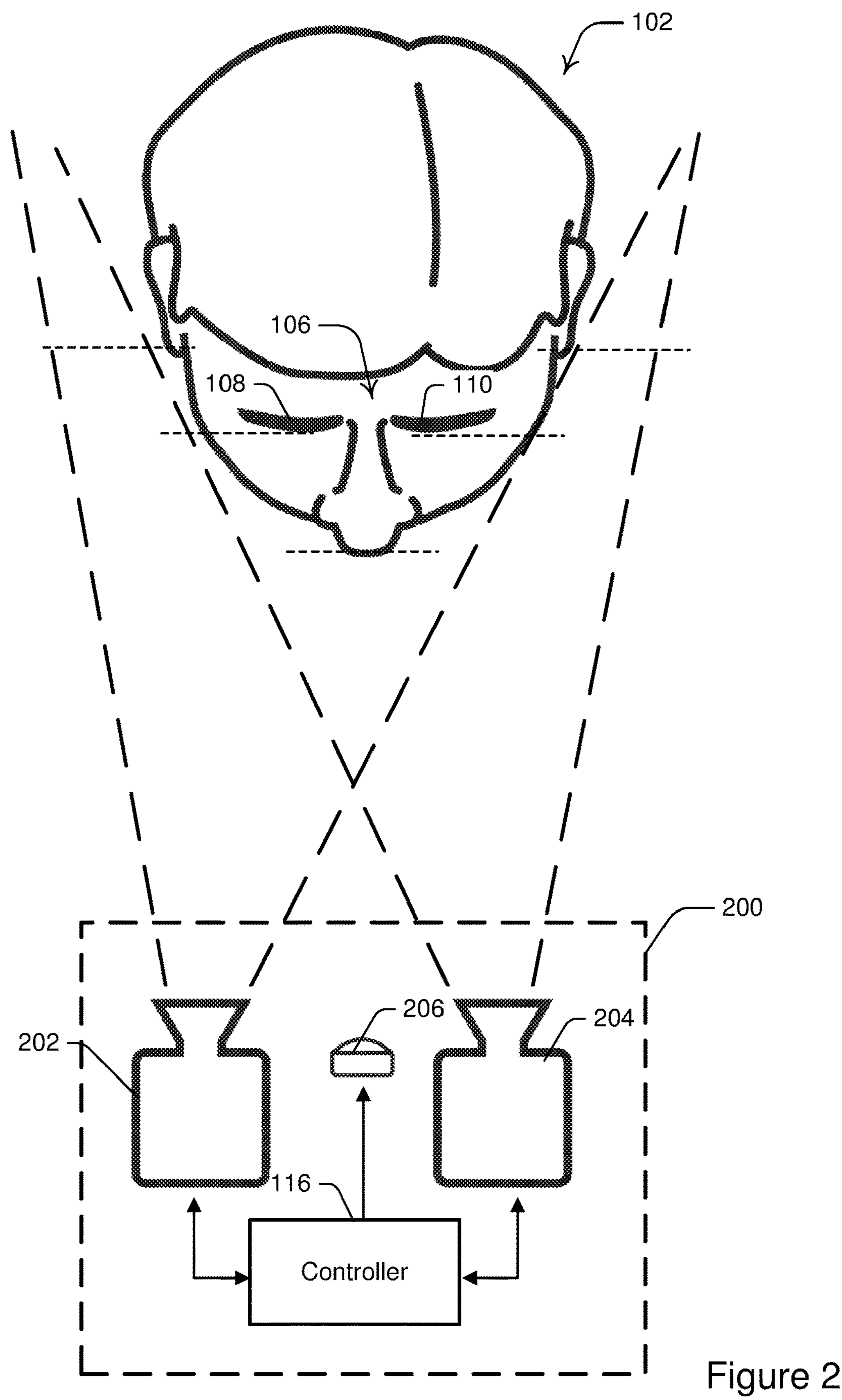
FIG. 2 is a schematic plan view of an eye gaze tracking system according to a second embodiment of the disclosure.

Although only a single time of flight camera is used in system 100, it will be appreciated that, in alternative embodiments, other systems of cameras are used to image a scene in three dimensions. By way of example, FIG. 2 illustrates an alternative gaze tracking system 200 which utilizes two conventional digital cameras 202 and 204 (in a stereoscopic arrangement) to image a single scene with their overlapping fields of view. Through appropriate calibration and identification of corresponding pixels between the two cameras, depth information can be extracted to image the scene in three dimensions. In further alternative embodiments (not illustrated), use is made of scanning range cameras or a single camera having capability to obtain depth information of the scene being images or at least sub-regions of the scene. It will further be appreciated that gaze tracking according to the present disclosure can be performed with systems implementing a combination of different cameras. For example, as time of flight cameras often have a lower resolution than conventional two dimensional digital cameras, one embodiment leverages the use of both a time of flight camera and a conventional digital camera. The general requirement for the camera system is that depth information can be obtained.

System 100 also includes two light sources in the form of light emitting diodes (LEDs) 112 and 114, which are configured to selectively illuminate the subject 102 during capture of the images. LEDs 112 and 114 preferably emit electromagnetic radiation in the infrared or near-infrared wavelength range outside the visible range to avoid distracting the subject. However, it will be appreciated that LEDs or other types of light sources operating in the visible or other wavelength range may be used. System 200 of FIG. 2 includes only a single infrared LED 206.

Control of the timing and operation of camera 104 and LEDs 112 and 114 is performed by a processor in the form of a controller 116. Depending on the system architecture and application, controller 116 may represent a microprocessor, personal computer, laptop computer tablet computer or smartphone. The skilled person will appreciate the controller 116 can be realized by any suitable processing hardware capable of high speed image processing. Controller 116 also includes or accesses non-transient memory for storing software instructions and algorithms for performing gaze tracking. These algorithms are described in detail below.

Controller 116 is configured to synchronously illuminate the subject 102 with light from one or both of LEDs 112 and 114 during image capture to improve the quality of the images and to generate useful corneal reflections as described below. System 100 leverages the two LEDs 112 and 114 symmetrically disposed about camera 104 to provide illumination from different angles. This advantageously allows for operating the system in high glare situations and also for generating multiple corneal reflections from the subject's eyes. It will be appreciated that, in other embodiments, gaze tracking systems according to the present disclosure include only a single LED (as in system 200 of FIG. 2) or more than two LEDs positioned in various spatial configurations.

Figure 3:
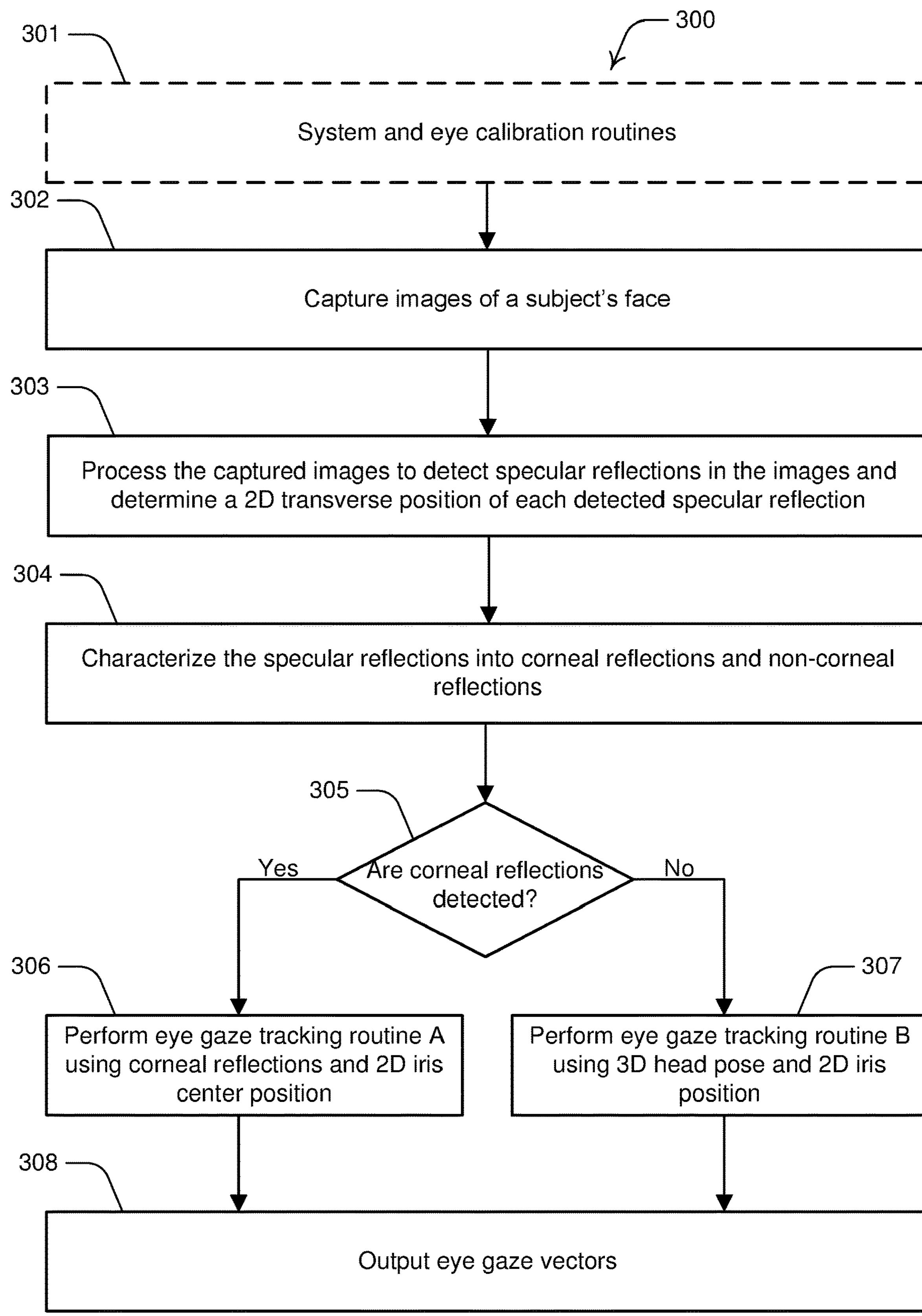
FIG. 3 is a process flow diagram illustrating the primary steps in a method of tracking a subject's gaze using a system of FIG. 1 or FIG. 2.

System 100 is configured to perform method 300 illustrated in the flow chart of FIG. 3 and the operation of system 100 will be described with reference this figure.

Initially, at step 301, system and eye calibration routines are performed to calibrate the system and also calibrate the eye tracking for a specific subject. The system calibration routine need only be performed once upon setup but is preferably performed regularly to re-calibrate the system to account for position drifting and other errors. The eye calibration routine calibrates for the subject's line of sight as each subject will possess a different ocular profile. The eye calibration routine subject-specific characteristics such as cornea size and the offset of the fovea from the optical axis. The eye calibration routine should be performed at least each time a new subject is to be tracked. However, if the system utilizes facial recognition, the eye calibration data can be stored in a database and loaded once the subject is recognized.

The system calibration routine involves determining a frame of reference and determining system parameters such as the relative positions between the camera 104 and LEDs 112 and 114 and the position and orientation between multiple cameras in multi-camera systems such as system 200. The system calibration also includes a depth calibration of the time of flight camera. This is typically performed by placing a calibration object in the field of view of the camera to be imaged for calibration. The calibration object is an object of dimensions known to a high degree of accuracy.

In the case of a stereoscopic camera system such as system 200, the two cameras first need to be calibrated by determining the relative position and orientation of the cameras relative to each other or a reference point to compute the ray intersection point for associated pixels of the cameras. Furthermore, there is a need to identify where each surface point that is visible in one stereo image is located in the other stereo image. The cameras must also be positioned so as to be capturing overlapping fields of view. Calibration of the scene can be initially performed by placing an object having a predefined calibration pattern in the scene to be imaged. Upon capturing stereo images, the calibration pattern can be used to identify corresponding pixels of the cameras and also to identify other parameters of the simulated 3D scene, such as the rotation and shift in three dimensions between the cameras, focal lengths, distortion etc. Using these parameters, the three dimensional coordinates of objects can be calculated within the scene.

The eye calibration routine involves prompting the subject to fixate their gaze on one or more points of known position relative to the camera. In one example, the subject may fixate on a set of reference LEDs which are disposed at different angular positions and which flash at different times while the camera 104 captures images of the subject. In another example, the subject may fixate on different known points on a display screen such as an LCD monitor. Extrapolation of the gaze vectors from the known gaze points allows for calibration of the unknown parameters in the system.

Under good conditions, a gaze tracking system estimates a gaze direction vector for both eyes of a subject. By determining where the gaze rays intersect, a subject's point of gaze (POG) can be deduced. Alternatively, if the subject is known to be viewing a plane such as a computer screen, the POG can be computed as the intersection of the gaze rays with the plane of the screen.

Figure 4:
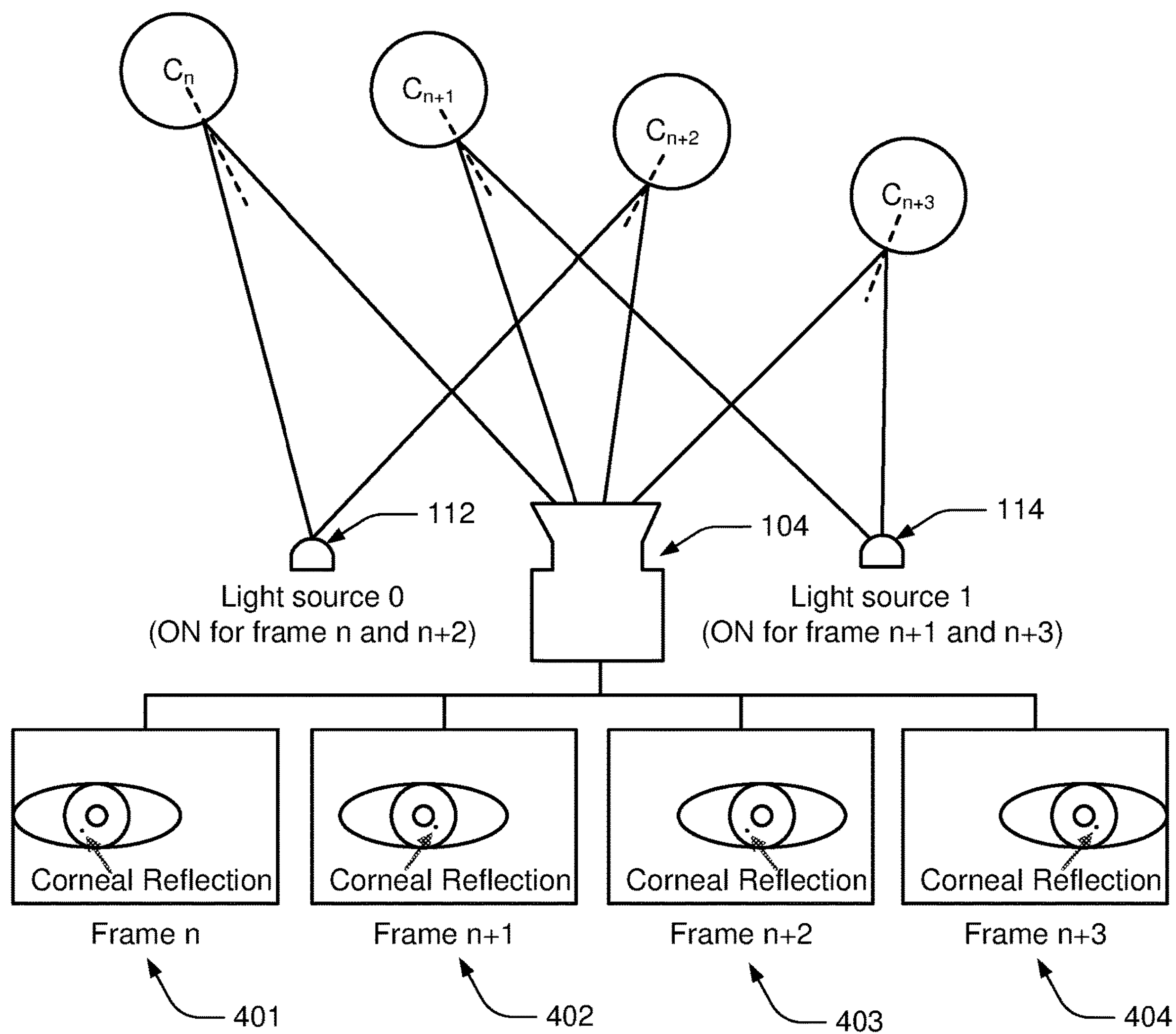
FIG. 4 is a schematic illustration of a processing arrangement for detecting corneal reflections from alternating light sources in a sequence of images.

After calibration is complete, at step 302, normal operation of the system commences and a sequence of time separated images are captured by camera 104. During the capture, the subject's eyeballs are illuminated by LEDs 112 and 114. Illumination of sequential frames is preferably provided by a different light source in an alternating fashion. As shown in FIG. 4, light source 0 (112) is ON for the even numbered image frames and light source 1 (114) is ON for the odd numbered image frames. In systems using more than two light sources, it is preferable that the illumination profile varies by at least one of the light sources each frame. By way of example, in a system including three light sources (L1, L2 and L3), consecutive image frames in the time series may be illuminated using the following illumination sequence:

Frame 1: L1+L2
Frame 2: L1+L3
Frame 3: L2+L3
Frame 4: L1+L2+L3
Frame 5: L1+L2 . . .

This sequencing is determined by controller 116. The timing of the illumination is synchronized with the capture of image frames in the sequence of images. The general preference is that there is some variation in illumination profile (different actuated light sources or combinations of actuated light sources) between consecutive frames of the time series to better differentiate the specular reflections from noise.

At step 303, controller 116 processes the captured images to detect specular reflections present in the images and determine a two dimensional position of any detected specular reflections. Given a triplet of frames Fn, Fn+1 and Fn+2 (401-403), a set of two dimensional glints Gn, Gn+1 and Gn+2 is extracted as two-dimensional coordinates of pixels within the image. Glint extraction can be done using well known computer vision methods, such as the maximum of Laplacian operators, each of which will be apparent to those skilled in the art. Those glints are either corresponding to a corneal reflection or any other specular reflection in the image. The number of glints detected within an image can range from a few to several hundred depending on the environment imaged and the lighting. In systems implementing multiple glint detection modules, the glint extraction process can be performed in parallel. Due to the small size of glints with an image, overlap of pixels between the separate modules can be significantly reduced.

At stage 304, controller 116 determines the detected specular reflections to be corneal reflections and non-corneal reflections (such as reflections from a subject's eyeglasses). In one embodiment, a motion model is applied to the image data or to subsets of the image data located around the subject's eyes. An exemplary motion model is a constant velocity model of an eye. Such a model applies location constraints on glints observed across different image frames. The location is constrained on the basis that, over the time difference between frames, the glints are only able to move a predetermined distance equal to a constant velocity multiplied by the time difference. Another exemplary motion model is an acceleration model of an eye which applies similar location constraints based on a modeled acceleration of an eye. Specular reflections which do not obey the applied model are assumed to be non-corneal reflections.

Ideally, a minimum of three image frames are used for constant velocity assumption filtering, or four frames for constant acceleration filtering. The embodiment described herein relates to a constant velocity model, but the skilled person will understand that extension to a constant acceleration or other motion models can be used. The model is applied by passing the captured image data through an algorithm run by controller 116. Each model applies constraints which relate to the typical motion of an eye. Corresponding motion models of other objects can be applied when tracking other objects within images.

It is necessary to consider whether any triplet of glints in consecutive frames is relevant. Where only one glint is picked per set Gn, Gn+1 and Gn+2, this involves trying to identify triplets corresponding to three consecutive corneal reflections on the same cornea. A first cull can occur at this stage to reject triplets where the glint position on two consecutive frames is greater than a predetermined threshold distance. For example, the threshold distance may be based on a distance derived by a maximum velocity of the cornea in three dimensional space. Assuming a known corneal radius R (which is very similar across the human population), a minimization process can then be performed to determine the best cornea trajectory in three dimensions (six degrees of freedom using a constant velocity model) that fit the triplet of glints (six observations from 3×two dimensional locations). Any iterative optimization process can be used at this stage (e.g. Levenberg-Marquardt) using the geometry illustrated in FIG. 5, which models the cornea 500 as a sphere positioned within a spherical eyeball 502 and offset from the center of eye rotation 504. For the illustrated embodiment, a specific fast solution to the optimization problem can be used.

Figure 5:
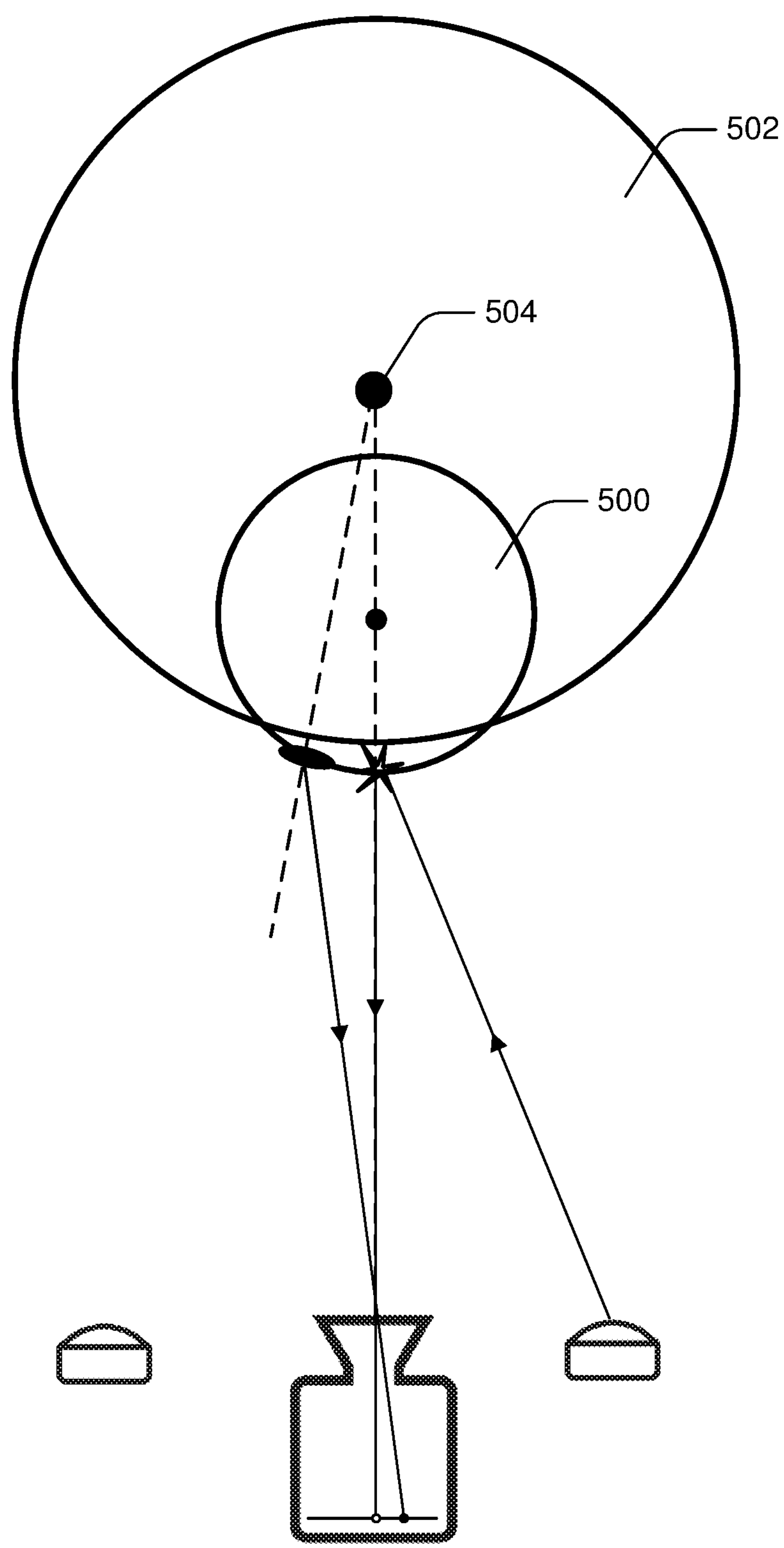
FIG. 5 is a schematic illustration of the geometry for determining eye positions in three dimensions using information from corneal reflections.

From a mathematical perspective, the trajectory of the cornea 500 can be computed from a sequence of two dimensional glint locations captured by a system as illustrated in FIG. 5, with the following considerations:

A camera/with known intrinsic projection parameters $\theta$. Typically the camera is modeled as having a pinhole aperture and a sensor array disposed along a defined image plane.

A reference frame F aligned with the camera axis (X,Y parallel to the image plane, Z collinear with the optical axis of the camera) and centered on the camera centre of projection.

An infrared LED located at a known three dimensional location L in the camera reference frame F.

A spherical cornea of known radius R, whose center is following a trajectory $C=\{C_1, \ldots, C_n\}$ in the reference frame F in a sequence of images.

A motion model $C_i=g(\alpha,i)$ where $\alpha$ are the motion parameters (e.g. constant velocity or constant acceleration) describing the trajectory C.

A sequence of two dimensional glints locations $G=\{G_1, \ldots, G_n\}$ corresponding to the reflections of the light emanating from the infrared illuminator on the surface of the cornea as imaged by the camera.

Using well known reflective geometry of spherical mirrors and projective geometry of cameras, there is a known function $\overline{G}_i=f(L, R, \alpha, \theta, i)$ where $\overline{G}_i$ is the theoretical location of the specular reflection $G_i$. The parameters of the cornea trajectory can then be computed by minimizing the error function:

$$\min_{\alpha}\sum_{i=1}^{n}(G_i-\overline{G}_i)^2$$

The minimum of this function can be found using well-known optimization techniques. Once the parameter $\alpha_{min}$ is found the trajectory T of the cornea can be computed using the known motion model.

Note that for simplification the cornea is assumed to be a sphere of known radius R. However, as mentioned above, the method remains valid for any other parametric shape of the cornea (e.g. ellipsoid) as long as the theoretical location $G_i$ of the glint can be computed from the known position (and optionally orientation) of the cornea. A number of different geometric models of the eye and cornea can be implemented into gaze tracking algorithms. Example models that can be implemented in the present disclosure are outlined in Villanueva, A., Cerrolaza, J. J. and Cabeza, R., 2008. *Geometry Issues of Gaze Estimation*. INTECH Open Access Publisher (hereinafter "Villeneuve et al.") and Hennessey, C., Noureddin, B. and Lawrence, P., 2006, March. *A single camera eye-gaze tracking system with free head motion*. In Proceedings of the 2006 symposium on Eye tracking research & applications (pp. 87-94). ACM (hereinafter "Hennessey et al."). The contents of these references are incorporated herein by way of cross-reference. Although the above process relies on two light sources to image two separate glints on the cornea, an equivalent process can be performed with system 200 of FIG. 2 where a single glint generated by single LED 206 is imaged at two angles on the cornea by cameras 202 and 204.

The above culling process will often reduce the number of candidate glints down to about three or four. For glints that pass the distance or trajectory assessment described above, the triplet of glints can then be rejected or accepted based on other predetermined criteria. For example, a maximum threshold on the residuals from the optimization (the error between the observed two dimensional positions of the glints and their optimized two dimensional positions computed from the optimized three dimensional cornea trajectory) can be set. Other thresholds on the optimized cornea trajectory can also be set, like the minimum and maximum depth or velocity of the cornea across multiple image frames.

The triplets that pass all the acceptance criteria are considered to be from actual corneal reflections and therefore both the two dimensional position of the eye and the three dimensional location of the cornea have been computed. In one embodiment, two consecutive glint triplets can then be assessed as a quadruplet using another motion model (e.g. constant velocity or constant acceleration) to further check for false positive detections.

The method detects any reflective object with a curvature similar to that of a cornea. It can also occasionally produce false positives in the presence of noise (high number of specular reflections) in the images. In such cases, further image analysis, like machine learning based classifiers or appearance based criteria, can be employed to eliminate unwanted false positives. There are several classes of classifier that could be used for this task. For example, support vector machine (SVM) or Random Forest classifiers using image features such as histogram of gradients (HOG) or convolutional neural network (CNN) using raw image pixel values can be used.

Finally, the eye position determined from the corneal reflections is output. The output data is in the form of either a three-dimensional coordinate of the cornea center position in the camera reference frame or a two-dimensional projection in the image. These coordinates are subsequently used in the gaze tracking routine described below to project the eye positions back onto the image or another image in the time series.

Stage 304 represents a determines corneal reflections to be useful glints from the corneas and other non-useful specular reflections. In some embodiments, further determination of the glints to be corneal or non-corneal glints can be performed to improve accuracy of the determination (at the expense of additional computer processing). By way of example, once a potential glint is detected, a 'shape regression' algorithm can be initiated which attempts to find the contour of the eye around the glint, including the eyelid and limbus (iris boundary). The output may be a confidence value indicative of the confidence that the glint corresponds to a corneal reflection. A threshold confidence value such as 0.7 may trigger whether to classify the glint as a corneal or non-corneal glint.

Several examples of shape regression are known, such as Supervised Descent Method (SDM) or Convolutional Neural Network (CNN). If the glint lies outside the limbus or the eyelids, then it can be deemed as a false positive. A similar shape regression algorithm could be performed to identify other facial features to estimate a confidence that the region around the facial landmarks has the appearance of a face.

Figure 6:
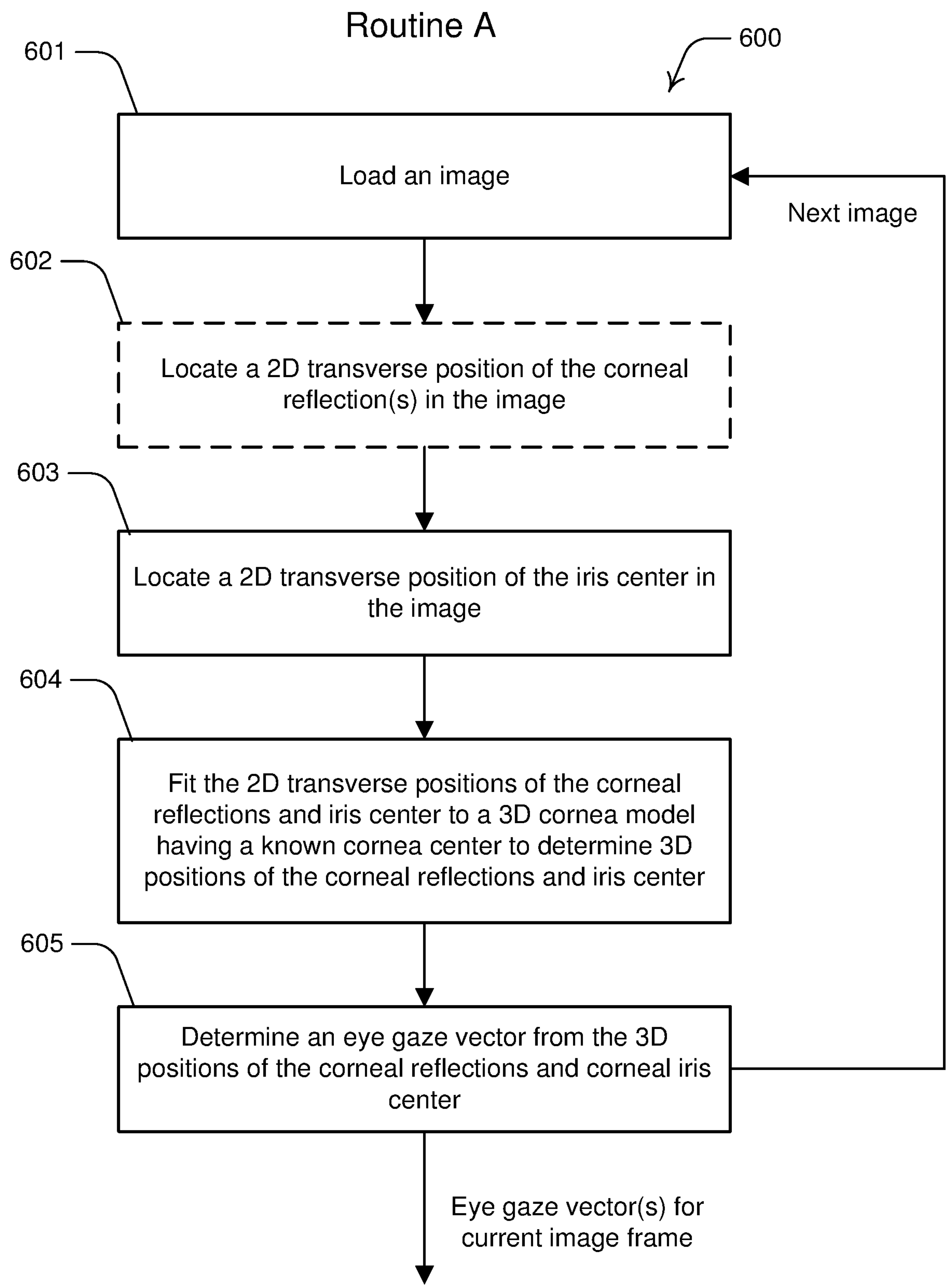
FIG. 6 is a process flow diagram illustrating the primary steps in a first gaze tracking routine using corneal reflections of light sources to determine eye position and gaze information.

If, at stage 305, one or more specular reflections are determined to be corneal reflections in stage 304, then control progresses to stage 306 where a first eye gaze tracking procedure (routine A) is performed on one or both eyes of the subject based on the relative positions of the at least one corneal reflection and at least one reference eye feature. The primary stages of eye gaze tracking routine A are illustrated in FIG. 6. A detailed description of routine A is set out below.

Figure 8:
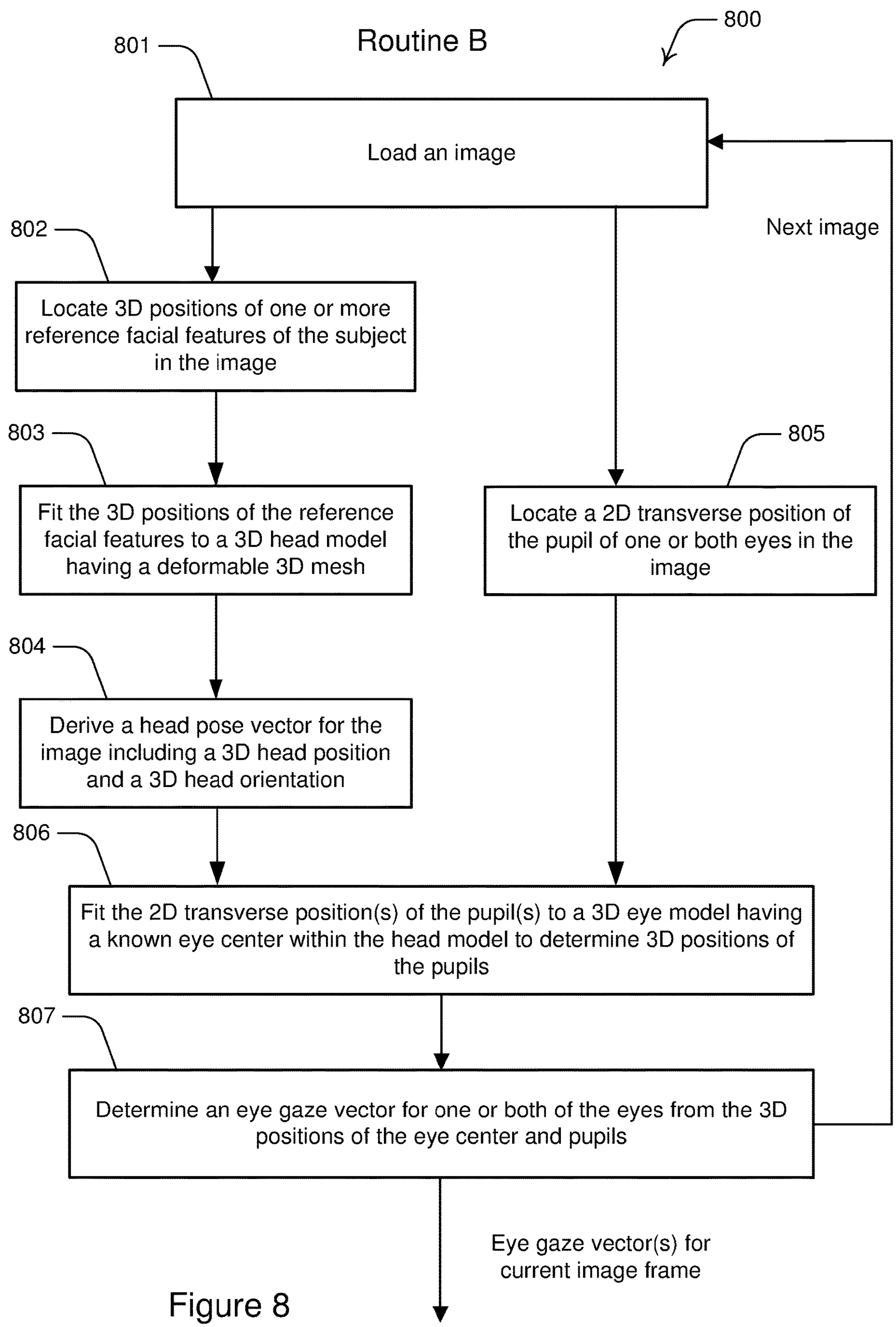
FIG. 8 is a process flow diagram illustrating the primary steps in a second gaze tracking routine using head pose information to determine eye position and gaze information.

If, at stage 305, no specular reflections are determined to be from corneal reflections, at stage 305, control progresses to stage 307 where a second eye gaze tracking procedure (routine B) is performed on one or both eyes of the subject based on the estimation of head pose of the subject. The primary stages of eye gaze tracking routine B are illustrated in FIG. 8. A detailed description of routine B is set out below.

Finally, at stage 308 eye gaze vectors of one or both eyes are output from the selected eye gaze tracking procedure. Each eye gaze tracking procedure is performed on a sequence of time separated images for a predetermined period of time. The output gaze vectors may be mapped onto images of the field of view of the subject to graphically illustrate the subject's gaze behavior. An application of the gaze tracking system is a driver monitoring system for a vehicle. The gaze tracking system can be integrated with a driver facing camera mounted in or relative to the vehicle dash. The determined gaze vectors can be mapped to a forward facing camera which shares the field of view of the driver. The gaze behavior can be used as an indicator of driver alertness and distraction to issue warnings.

Eye Gaze Tracking Routine A—Using Detection of Corneal Reflections ('Glints')

In eye gaze tracking routine A, eye gaze direction is calculated by detecting the three dimensional position of corneal reflections of the light source in conjunction with detecting the two dimensional position of one or more reference eye features such as a pupil center, iris center, pupil/iris boundary, iris/sclera boundary, eyelids or eye corners. For ease of understanding, the following description will be provided using the iris center as the reference eye feature. However, it will be appreciated that an equivalent method can be performed using any other suitable reference eye feature. In some embodiments, positions of more than one reference eye feature can be determined to reduce errors at the cost of additional processing resources. Typically, iris boundaries are simpler to detect than pupil boundaries due to their larger size and therefore greater pixel coverage. However, Irises are often clipped by the eyelids and so, in certain circumstances, it is preferable or advantageous to use the pupil boundaries to estimate iris or pupil center, or another reference eye feature.

An exemplary embodiment method 600 of routine A is illustrated in FIG. 6.

Initially, at stage 601 a current image is loaded for processing. Method 600 may be performed sequentially on a batch of buffered images stored in memory or may be performed on an image-by-image basis as they are captured by camera 104.

As a precursor to determining corneal reflections from other specular reflections in stage 304 included modeling the cornea and determining the three dimensional position of the cornea, some of the processing of method 600 has already been completed. However, in embodiments where the determination of specular reflections is simpler or does not require the determination of a position of corneal reflections, stage 602 is performed where two dimensional positions of the corneal reflection(s) can be determined in a captured image. Although initially two or more corneal reflections are required for calibration, during active tracking, only a single corneal reflection is required to be identified, in combination with the pupil or iris center.

Next, at stage 603, a two dimensional position of the iris centre is determined in a captured image. Iris and pupil detection can be performed from a number of methods known in the art including detecting known features of eyes and identifying the pupil based on shape recognition or edge detection. Pupil or iris detection typically involves performing edge detection around the iris/sclera boundary or pupil/iris boundary to identify points along the pupil or iris perimeter. The iris/pupil center can then be extrapolated by assuming a circular or elliptical pupil/iris shape model. Fitting the pupil/iris perimeter points to the shape model (for example with a circular Hough transform) determines an iris/pupil center position. Other known pupil and iris detection methods are known and can be used within the scope of the present disclosure. A circular Hough transform process is explained in detail in Ioannou, D., Huda, W. and Laine, A. F., 1999. *Circle recognition through a 2D Hough transform and radius histogramming.*, Image and vision computing, 17(1), pp. 15-26.

At stage, 604, the two dimensional positions of the corneal reflections and the pupil position are fitted to a three dimensional cornea model having a known cornea center and pupil position to determine three dimensional positions of the corneal reflections and pupil center. Where the determination stage 304 utilized a corneal model, this model can be used in stage 604. However, for the following description, the model described in Hennessey et al. will be used, which is reproduced in FIG. 7.

Figure 7:
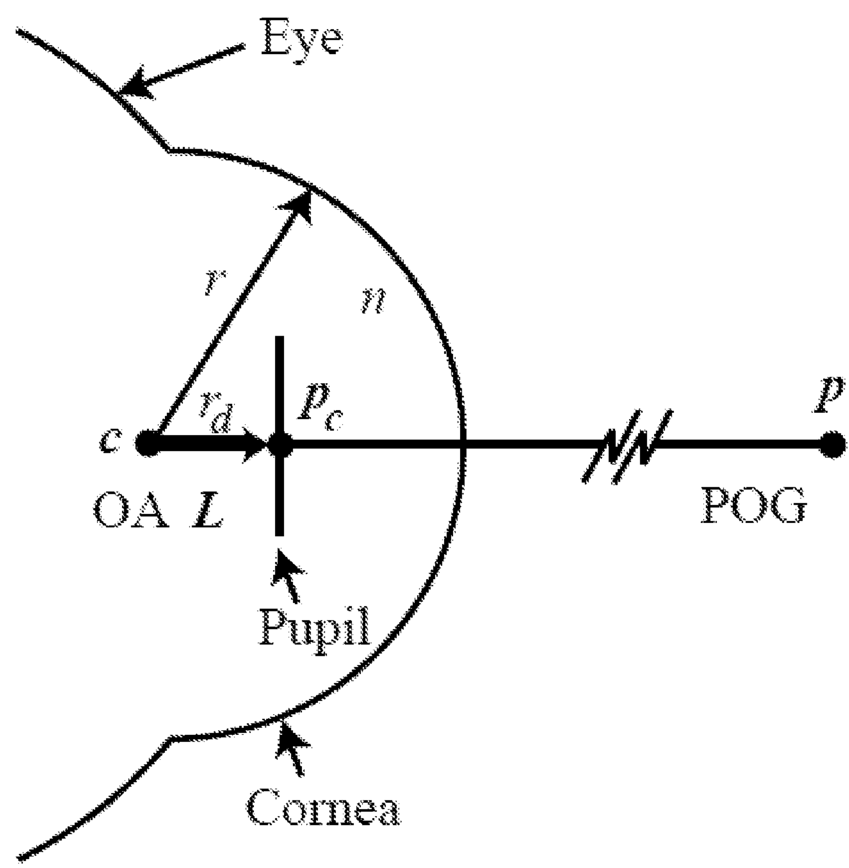
FIG. 7 is a schematic drawing of an exemplary corneal model and its associated geometry used to calculate eye gaze vectors.

FIG. 7 illustrates a simplified eye model with the parameters of interest, r (radius of the cornea), $r_d$ (distance from the center of the cornea to the center of the pupil), and n (refractive index of the aqueous humor, and the points $p_c$ and c, which are required to compute the optical axis (OA) vector L. The OA is defined as the vector from the center of the cornea c to the center of the pupil $p_c$. The POG p is the intersection of the OA with the object being viewed. If the subject is not viewing a known plane such as a computer monitor, this POG can be computed as the intersection of the gaze rays of both eyes.

The OA is different from a subject's line of sight (LOS) which is the vector that traces from the fovea (high acuity portion of the retina) through the center of the pupil and ultimately to the real POG. The location of the fovea varies from person to person, and can be located several degrees from the OA. The offset between the estimated POG and the real POG due to the difference between the OA and the LOS is fixed for each subject and is compensated for by the eye calibration routine performed initially.

As described above in relation to characterizing stage 304, to determine the cornea center c, the two dimensional image locations of two glints off the surface of the cornea are fitted to the eye model (i.e. from two or more light sources). Where the light sources are activated in a strobe pattern on successive images, the glint position from temporally adjacent images can be combined. Using multiple glints provides for triangulating the three dimensional cornea center in the frame of reference of the camera.

With the three dimensional position of the cornea center c known, the three dimensional position of the iris/pupil center can be extrapolated by tracing two dimensional points of the pupil or iris boundary (determined in stage 603) from the camera sensor to the surface of the cornea and applying model constraints such as Snell's law to account for refraction through the aqueous humor. Models of greater or lesser complexity can be used, each with greater or fewer parameters to be estimated by applying additional constraints.

Once the three dimensional position of the iris/pupil center $p_c$ and glints are known, the eye gaze vector can be calculated as the vector L between $p_c$ and c for a current image frame. The gaze vectors for one or both eyes are output at stage 605. The procedure repeats for subsequent images in the sequence (or a select subset of the images). Routine A can be performed simultaneously and independently on one or both eyes detected in each image. Where gaze rays for both eyes can be detected in an image, the POG can be estimated as the point of intersection of the two gaze rays. Where no eyes are detected the system can be configured to skip that image frame.

It will be appreciated that other known gaze tracking routines utilizing detection of glint position can be equivalently used in place of exemplary method 600.

Eye Gaze Tracking Routine B—Using 3D Head Pose

In eye gaze tracking routine B, eye gaze tracking is performed using a method to first estimate the three dimensional head pose of the subject and subsequently estimate eye gaze direction from the head pose. A related method performed in a stereoscopic camera system is outlined in Edwards et al. In describing the present disclosure, a similar process to Edwards et al. will be followed. The subject matter of Edwards et al. is incorporated herein by way of cross reference.

An exemplary method 800 of routine B is illustrated in FIG. 8.

Initially, at stage 801 a current image is loaded for processing. Like method 600, method 800 may be performed sequentially on a batch of buffered images stored in memory or may be performed on an image-by-image basis as they are captured by camera 104.

At stage 802 the image is processed to identify reference facial features such as eye corners, nostrils, mouth corners, ears or any other small recognizable areas on the face, and extract the three dimensional positions of those features. The features are preferably identified by cross-correlating the image data with stored feature templates. The stored templates may represent, for example, shapes of eyes captured at different angles with respect to the camera. The templates may be two or three dimensional datasets. To improve processing, the cross correlation process may be limited to regions of the images where features are expected to lie. The expected positions of features can be derived from their positions in past images.

Preferably both eyes and one or more other facial features can be identified within an image. Once a suitable number of facial features are identified, the three dimensional positions of the facial features are fitted to a three dimensional model of a head at stage 803. The head model is formed of a mesh structure that is deformable to account for the different profiles of individuals.

The features are fit or mapped onto the head model through a best fit method such as least squares, linear regression or the like. The head pose is determined in three dimensions as a combination of two sets of coordinates: rotation (θ, φ, φ); and translation (x, y, z). The optimal computed head pose (consisting of a rotation and a translation component), is that which best maps the head model to the facial feature using three dimensional measurements. In one embodiment, the strength of correlation of each template is used as a weight in a least-squares minimization procedure.

The rotation R and translation T of the head model can be recovered by minimizing the error E defined by:

$$E=\Sigma_{i=0}^{n-1} w_i \|x_i - Rm_i - T\|^2,$$

where $w_i$ is the confidence measurement of the ith feature, $x_i$ is the measured three dimensional position of the ith feature and $m_i$ is the three dimensional position of this feature in the face model.

In Edwards et al. the head model is constructed from a predetermined average human head size. As human head sizes can vary by as much as 10%, this approximation can result in head pose errors. In the present disclosure, use of a time of flight camera allows for obtaining full depth information of the entire face and head profile of the subject to more accurately determine the subject's head size. The additional depth information can be fed to the deformable head model to factor this scale size during the fitting process.

Once the head pose optimization routine is complete, the optimum current head pose vector is output at stage 804.

In conjunction with the head pose estimation of stage 803, the image is processed at stage 805 to determine a two dimensional position of a pupil or iris of one or both of the subject's eyes. Pupil/iris detection can be performed in a similar manner to that described above for stage 603. For example, the pupil center position is determined by identifying points along the pupil/iris perimeter and extrapolating a pupil center position by fitting the perimeter to a circular or elliptical pupil/iris shape model.

Next, at stage 806, the two dimensional pupil positions of one or both eyes are fitted to respective three dimensional eye models. In one embodiment, the eyes are modeled as being spherical and having known radii r and centers of rotation e within the three dimensional head model. The pupil position p computed from stage 805 is assumed to lie on the surface of the spherical eye at distance r from the center of rotation e. Thus, the head pose vector (including three dimensional position and orientation) determined in stage 804 is used to determine a three dimensional position of one or both eyes. By fitting the two dimensional pupil positions to the eye model and applying the model constraints, the three dimensional pupil position can be determined as follows.

Initially the three dimensional position e of the eyeball centre (left or right) is calculated by using the relation $$e=Re_m+T,$$

where $e_m$ is the calibrated three dimensional position of the eyeball centre in the head model and R and T are the recovered rotation and translation of the head from the head pose of stage 804.

Figure 9:
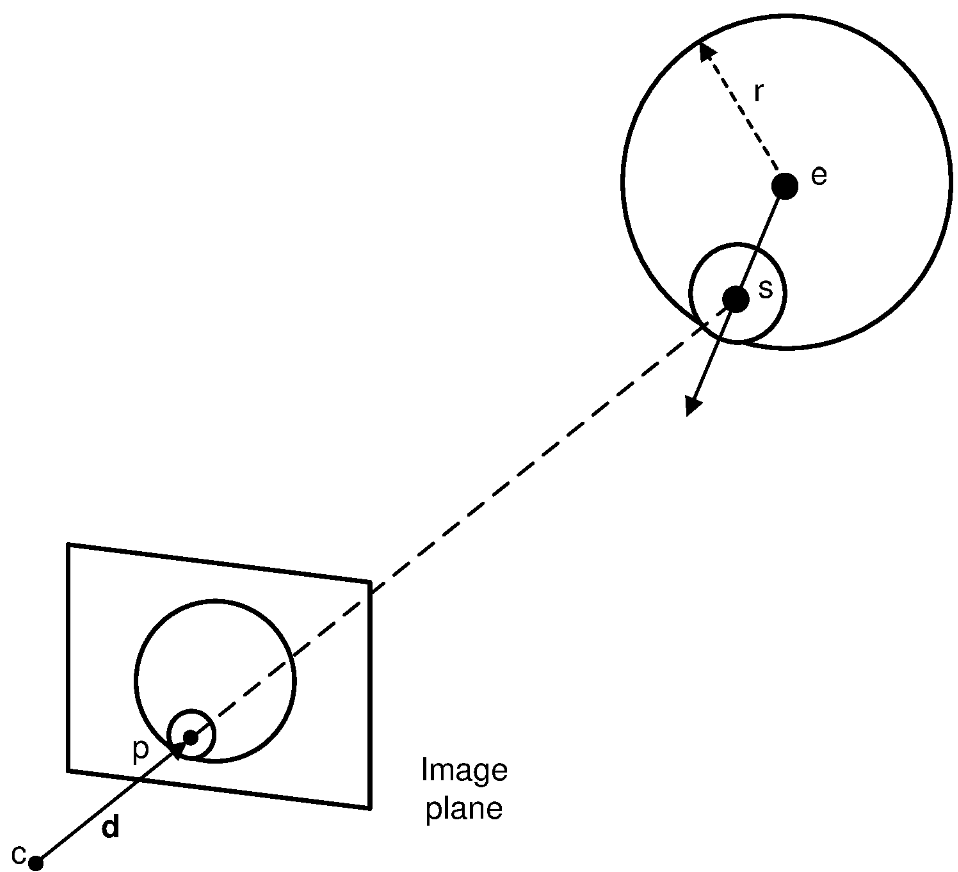
FIG. 9 is a schematic illustration of the geometry for determining a gaze direction vector using the head pose based gaze tracking routine of FIG. 8.

With reference to FIG. 9, once the centre p of the pupil has been located in the image, a direction vector d can be computed pointing from the camera centre position toward an actual iris/pupil center s. The gaze direction is then given by direction of the vector es. The 3D coordinate s can be computed by solving the equation $$s=c-[d\cdot ec+\sqrt{(d\cdot ec)^2-\|ec\|^2+r}]d.$$

Thus, by solving the above equation, the three dimensional position of both the eye center of rotation e and the pupil/iris center s are known and the gaze direction vector es for each eye is output at stage 807. Method 800 can be performed simultaneously and independently on each eye.

The visibility of each eye is determined using the head-pose measurement. When both eyes are visible, method 800 is performed on both eyes and the eye gaze direction can be computed as the average direction of both eyes. When only one eye is visible, the gaze direction is computed using only the visible eye. When no eyes are visible, the gaze direction can be computed as the direction perpendicular to the plane of the subject's face from the three dimensional head pose measurement.

CONCLUSIONS

The present disclosure provides a hybrid eye tracking system and method in which different eye tracking routines are performed based on factors such as the presence of corneal reflections in the captured images. The disclosure provides a robust method to track a subject's eyes under a variety of lighting and eye gaze conditions and flexibility to adjust the eye tracking to suit particular requirements (resolution, lighting etc.).

The eye gaze routine B does not rely on corneal reflections allowing the image processing to be performed at much lower image resolutions (i.e. by sub-sampling the captured images or reducing the camera image capture resolution). Routine B can also be performed under much more relaxed lighting conditions as corneal reflections are not required. Thus, the system can operate at lower LED power or with no LEDs at all.

In cases where corneal glints are detected, the information obtained from both gaze computation routines A and B for a more robust estimation of the gaze.

Interpretation

Unless specifically stated otherwise, as apparent from the following discussions, it is appreciated that throughout the specification discussions utilizing terms such as "processing," "computing," "calculating," "determining", analyzing" or the like, refer to the action and/or processes of a computer or computing system, or similar electronic computing device, that manipulate and/or transform data represented as physical, such as electronic, quantities into other data similarly represented as physical quantities.

In a similar manner, the term "controller" or "processor" may refer to any device or portion of a device that processes electronic data, e.g., from registers and/or memory to transform that electronic data into other electronic data that, e.g., may be stored in registers and/or memory. A "computer" or a "computing machine" or a "computing platform" may include one or more processors.

The methodologies described herein are, in one embodiment, performable by one or more processors that accept computer-readable (also called machine-readable) code containing a set of instructions that when executed by one or more of the processors carry out at least one of the methods described herein. Any processor capable of executing a set of instructions (sequential or otherwise) that specify actions to be taken are included. Thus, one example is a typical processing system that includes one or more processors. Each processor may include one or more of a CPU, a graphics processing unit, and a programmable DSP unit. The processing system further may include a memory subsystem including main RAM and/or a static RAM, and/or ROM. A bus subsystem may be included for communicating between the components. The processing system further may be a distributed processing system with processors coupled by a network. If the processing system requires a display, such a display may be included, e.g., a liquid crystal display (LCD) or a cathode ray tube (CRT) display. If manual data entry is required, the processing system also includes an input device such as one or more of an alphanumeric input unit such as a keyboard, a pointing control device such as a mouse, and so forth. The term memory unit as used herein, if clear from the context and unless explicitly stated otherwise, also encompasses a storage system such as a disk drive unit. The processing system in some configurations may include a sound output device, and a network interface device. The memory subsystem thus includes a computer-readable carrier medium that carries computer-readable code (e.g., software) including a set of instructions to cause performing, when executed by one or more processors, one of more of the methods described herein. Note that when the method includes several elements, e.g., several stages, no ordering of such elements is implied, unless specifically stated. The software may reside in the hard disk, or may also reside, completely or at least partially, within the RAM and/or within the processor during execution thereof by the computer system. Thus, the memory and the processor also constitute computer-readable carrier medium carrying computer-readable code.

Reference throughout this specification to "one embodiment", "some embodiments" or "an embodiment" means that a particular feature, structure or characteristic described in connection with the embodiment is included in at least one embodiment of the present disclosure. Thus, appearances of the phrases "in one embodiment", "in some embodiments" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

In the claims below and the description herein, any one of the terms comprising, comprised of or which comprises is an open term that means including at least the elements/features that follow, but not excluding others. Thus, the term comprising, when used in the claims, should not be interpreted as being limitative to the means or elements or stages listed thereafter. For example, the scope of the expression a device comprising A and B should not be limited to devices consisting only of elements A and B. Any one of the terms including or which includes or that includes as used herein is also an open term that also means including at least the elements/features that follow the term, but not excluding others. Thus, including is synonymous with and means comprising.

It should be appreciated that in the above description of exemplary embodiments of the disclosure, various features of the disclosure are sometimes grouped together in a single embodiment, Fig., or description thereof for the purpose of streamlining the disclosure and aiding in the understanding of one or more of the various inventive aspects. This method of disclosure, however, is not to be interpreted as reflecting an intention that the claims require more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those skilled in the art. For example, in the following claims, any of the claimed embodiments can be used in any combination.

In the description provided herein, numerous specific details are set forth. However, it is understood that embodiments of the disclosure may be practiced without these specific details. In other instances, well-known methods, structures and techniques have not been shown in detail in order not to obscure an understanding of this description.

Similarly, it is to be noticed that the term coupled, when used in the claims, should not be interpreted as being limited to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B which may be a path including other devices or means. "Coupled" may mean that two or more elements are either in direct physical, electrical or optical contact, or that two or more elements are not in direct contact with each other but yet still co-operate or interact with each other.

Thus, while various embodiments have been described, those skilled in the art will recognize that other and further modifications may be made thereto without departing from the spirit of the disclosure, and it is intended to claim all such changes and modifications as fall within the scope of the disclosure. For example, any formulas given above are merely representative of procedures that may be used. Functionality may be added or deleted from the block diagrams and operations may be interchanged among functional blocks. Stages may be added or deleted to methods described within the scope of the present disclosure.

We claim:

1. A processor-implemented method of determining eye gaze vectors of a subject, the method comprising:

capturing, by one or more imaging devices, a sequence of time separated images of the subject's face including one or both of the subject's eyes;

processing, by a processor circuit, the images to detect specular reflections present in the images, and to determine two dimensional positions of detected specular reflections;

determining, from the detected specular reflections, a presence or absence of corneal reflections and non-corneal reflections;

upon determination of at least one corneal reflection, performing a first eye gaze tracking procedure based on relative positions of the at least one corneal reflection and at least one reference eye feature;

upon determination of an absence of corneal reflections, determining one or more three dimensional positions of respective one or more reference facial features of the subject, and performing a second eye gaze tracking procedure on one or both eyes of the subject based on an estimation of a head pose of the subject based on the three dimensional positions of the one or more detected reference facial features; and determining, based on the first or second eye gaze tracking procedure, eye gaze vectors for one or both eyes.

2. The method according to claim 1, wherein the at least one reference eye feature includes one or more of a pupil center, an iris center, a pupil/iris boundary, or an iris/sclera boundary.

3. The method according to claim 1, wherein the one or more reference facial features of the subject includes one or more of a pupil center, an iris center, a pupil/iris boundary, an iris/sclera boundary, eyelids, eye corners, mouth corners, nostrils, and ears of the subject.

4. The method according to claim 1, wherein determining a corneal reflection includes monitoring the two dimensional positions of the specular reflections in the sequence of images and determining the detected specular reflections to be corneal reflections when a change in position of the specular reflections between two or more time separated images is less than or equal to a predetermined distance.

5. The method according to claim 1, wherein the first eye gaze tracking procedure comprises:

determining a two dimensional position of at least one reference eye feature;

fitting one or more two dimensional positions of one or more respective corneal reflections, and fitting the at least one reference eye feature, to a three dimensional cornea model having a known cornea center, to thereby determine three dimensional positions of the one or more corneal reflections, and a three dimensional position of an iris center; and determining eye gaze vectors for one or both eyes from the three dimensional positions of the one or more corneal reflections, and three dimensional position of the at least one reference eye feature.

6. The method according to claim 1, wherein the second eye gaze tracking procedure comprises:

fitting the three dimensional positions of the one or more reference facial features to a three dimensional head model;

determining a head pose of the subject that includes a three dimensional position and a three dimensional orientation of the subject's head;

determining a two dimensional position of at least one reference eye feature of one or both eyes of the subject;

fitting the two dimensional position of the at least one reference eye feature to a three dimensional eye model having a known eye center, within the three dimensional head model, to determine a three dimensional position of the at least one reference eye feature;

determining an eye gaze vector for one or both of the eyes from the three dimensional position of the at least one reference eye feature and a three dimensional position of the known eye center.

7. The method according to claim 6, further comprising estimating the subject's head size from image depth information based on the three dimensional head model.

8. The method according to claim 1, wherein the one or more imaging devices includes a time of flight camera.

9. The method according to claim 8, wherein the time of flight camera outputs three dimensional image data, and two dimensional position data is obtained directly from the three dimensional image data.

10. The method according to claim 1, wherein the one or more imaging devices includes a single camera capable of estimating depths of features in images.

11. The method according to claim 1, further comprising an initial camera calibration that calibrates a position and an orientation of the one or more imaging devices.

12. The method according claim 5, including an initial eye calibration that calibrates the gaze vectors to account for a fovea offset and/or to account for a corneal radius of the subject.

13. The method according to claim 12, wherein the initial eye calibration includes capturing images of the subject's face while the subject is observing one or more reference points having one or more respective known three dimensional positions relative to the one or more imaging devices.

14. The method according to claim 13, wherein the initial eye calibration is performed using greater than five reference points.

15. The method according to claim 1, further comprising determining which eye gaze tracking procedure to use based on one or more factors.

16. The method according to claim 15, wherein the one or more factors include a confidence value indicative of a confidence that the detected specular reflection is a corneal reflection.

17. The method according to claim 15, wherein the one or more factors include a confidence value indicative of a confidence that a region around a corneal reflection has an appearance of an eye.

18. The method according to claim 15, wherein the one or more factors include a confidence value indicative of a confidence of the head pose.

19. The method according to claim 15, wherein the one or more factors include a confidence value indicative of a confidence that the region around facial landmarks has an appearance of a face.

20. A system configured to determine eye gaze vectors of a subject, the system comprising:

one or more imaging devices configured to capture a sequence of time separated images of the subject's face including one or both of the subject's eyes; and a processor circuit configured to:

process the images to detect specular reflections present in the images;

determine, from the detected specular reflections, a presence or absence of corneal reflections and non-corneal reflections;

upon determination of at least one corneal reflection, determine a two dimensional position of at least one corneal reflection and a two dimensional position of at least one reference eye feature of the subject, and perform a first eye gaze tracking procedure based on relative positions of the at least one corneal reflection and the at least one reference eye feature;

upon determination of an absence of corneal reflections, determine one or more three dimensional positions of respective one or more reference facial features of the subject, and perform a second eye gaze tracking procedure on one or both eyes of the subject based on an estimation of a head pose of the subject based on the three dimensional positions of the one or more reference facial features; and determine, based on the first or second eye gaze tracking procedure, eye gaze vectors.

* * * * *